United States Patent
Crisanti et al.

[11] Patent Number: 5,925,681
[45] Date of Patent: Jul. 20, 1999

[54] BLOOMING, DISINFECTANT CONCENTRATE COMPOSITIONS

[75] Inventors: Michael George Crisanti, Danbury, Conn.; Dennis Thomas Smialowicz, Waldwick, N.J.

[73] Assignee: Reckitt & Colman Inc., Wayne, N.J.

[21] Appl. No.: 08/944,992

[22] Filed: Oct. 7, 1997

[30] Foreign Application Priority Data

Mar. 1, 1997 [GB] United Kingdom .................. 9704285

[51] Int. Cl.$^6$ .......................... A01N 33/00; A01N 33/12; C11D 3/48; C11D 1/66
[52] U.S. Cl. .......................... 514/643; 514/642; 514/722; 514/724; 514/739; 514/772; 514/625; 514/627; 514/629; 514/937; 514/938; 514/939; 514/940; 514/941; 514/942; 514/943; 514/970; 514/973; 514/975; 422/28; 510/367; 510/382; 510/383; 510/384
[58] Field of Search .................. 514/642–643, 514/772, 722, 724, 739, 625, 627, 629, 937–943, 970, 973, 975; 422/28; 510/367, 382, 383, 384, 385, 391

[56] References Cited

U.S. PATENT DOCUMENTS

| | | | |
|---|---|---|---|
| 3,539,520 | 11/1970 | Cantor et al. | 510/391 |
| 4,040,989 | 8/1977 | Renaud et al. | 510/237 |
| 4,203,872 | 5/1980 | Flanagan | 510/67 |
| 4,272,395 | 6/1981 | Wright | 510/423 |
| 4,492,646 | 1/1985 | Welch | 510/423 |
| 4,504,505 | 3/1985 | Frazier | 426/482 |
| 4,511,488 | 4/1985 | Matta | 510/421 |
| 4,576,738 | 3/1986 | Colodney et al. | 510/424 |
| 4,704,225 | 11/1987 | Stoufer | 510/417 |
| 4,966,724 | 10/1990 | Culshaw et al. | 510/434 |
| 4,983,317 | 1/1991 | Requejo et al. | 510/419 |
| 5,244,666 | 9/1993 | Murley | 424/405 |
| 5,254,290 | 10/1993 | Blandiaux et al. | 510/417 |
| 5,281,354 | 1/1994 | Faber | 510/397 |
| 5,358,667 | 10/1994 | Bergmann | 510/122 |
| 5,454,984 | 10/1995 | Graubart et al. | 510/384 |
| 5,474,713 | 12/1995 | Faber | 134/42 |
| 5,591,708 | 1/1997 | Richter | 510/463 |

FOREIGN PATENT DOCUMENTS 2 304 728 3/1997 United Kingdom .

OTHER PUBLICATIONS

Copy of GB Search Report for GB Application No. 9704285.7 dated May 14, 1997.

*Primary Examiner*—John Pak
*Attorney, Agent, or Firm*—Fish & Richardson P.C.

[57] ABSTRACT

Concentrated aqueous liquid disinfectant compositions which exhibit a blooming effect when diluted in a larger volume of water are provided. The concentrate compositions include non-phenolic constituents to provide a disinfecting effect, and are non pine-oil containing. Working strength dilutions of the concentrated aqueous liquid disinfectant compositions are effective against gram positive type pathogenic bacteria such as *Staphylococcus aureus*, as well as gram negative type pathogenic bacteria such as *Salmonella choleraesuis*.

32 Claims, No Drawings

BLOOMING, DISINFECTANT CONCENTRATE COMPOSITIONS

The present invention relates to disinfectant compositions. More particularly the present invention relates to concentrated liquid disinfectant compositions which are normally diluted in a larger volume of water to form a working solution therefrom, and which exhibit a blooming effect when diluted.

Blooming is a property exhibited by dilutable compositions such as known cleaning compositions, specifically pine-oil type cleaning compositions which contain a significant amount (generally at least about 5% and more) of pine oil. Certain phenolic disinfectant compounds, such as LYSOL® disinfectant concentrate (Reckitt & Colman, Inc., Montvale N.J.) also exhibit such a blooming property. Blooming may be characterized as the formation of milky, creamy or cloudy appearance which is manifested when a dilutable composition is added to a larger volume or quantity of water. Blooming is an important characteristic from a consumer standpoint as it provides a visual indicator and impression to the consumer that the concentrated product contains active cleaning and/or disinfecting constituents which are released upon addition of the concentrate to a volume of water. Such is an important visual indicator of apparent efficacy of a concentrated product.

While presently commercially available materials have advantageous features, they are not without their attendant shortcomings as well. For example, the use of pine oil, and its pungent characteristic odor is frequently not desired. Also, such compositions frequently are directed to providing a cleaning effect, and do not provide an appreciable sanitizing effect.

Accordingly it is an object of the invention to provide an aqueous concentrated liquid disinfectant composition which comprises the following constituents:

(A) a volatile hydrophobic solvent;

(B) a hydrophilic solvent which stabilizes the volatile hydrophobic solvent;

(C) a nonionic surfactant having a HLB value of between about 10 and about 15, such as ethoxylated and/or propoxylated fatty alcohols, or ethylene oxide and/or propylene oxide block copolymers (D) a combination of (D1) a fatty alcohol alkoxylate having 2–3 moles of ethoxylation and/or propoxylation and HLB value of between 7 and 9, with, (D2) an alkanolamide wherein the ratio of (D1):(D2) is 1–10:1, preferably 3.0–5.0:1; and more preferably about 4.2:1

(E) a non-phenolic compound which is effective in providing a germicidal effect;

(F) a hydrotrope;

(G) water.

(H) one or more optional constituents including preservatives, fragrances, coloring agents, thickeners, pH adjusting agents, chelating agents, buffers, and cloud point modifiers.

It is a further object of the invention to provide such a concentrated liquid disinfectant composition wherein the composition exhibits a blooming effect when diluted in a larger volume of water.

It is a yet further object of the invention to provide such a concentrated liquid disinfectant composition wherein the composition exhibits a germicidal effect in both its concentrated form, and in an aqueous diluted form.

It is a still further object of the invention to provide such a concentrated liquid disinfectant composition which in a diluted form provides disinfection of surfaces wherein the presence of gram positive type pathogenic bacteria such as *Staphylococcus aureus,* and/or the presence of gram negative type pathogenic bacteria such as *Salmonella choleraesuis* and/or *Pseudomonas aeruginosa* is suspected.

It is a still further object of the invention to provide working solutions formed from concentrated liquid disinfectant compositions which exhibit a blooming effect when diluted in a larger volume of water.

It is among the further object of the invention to provide such a concentrated liquid disinfectant composition wherein the composition exhibits good long term stability, i.e., shelf stability in its concentrated form.

The concentrate compositions of the invention include a volatile hydrophobic solvent as constituent (A). Useful are hydrophobic solvents which find use in the present inventive compositions include: alcohols, aromatic solvents, esters, ethers, ketones, aldehydes, 1,1,1-trichloroethane, glycol ethers, perchloroethylene, certain volatile silicones such as polydimethylsiloxane, cyclohexanone, cyclohexanol, methylene chloride, mineral spirits, $C_6$–$C_{12}$ alkanes, $C_6$–$C_{12}$ alkenes, and particularly mineral spirits, as well as hexane or heptane. Other hydrophobic solvents exhibiting the characteristics denoted above and known to the art may also be utilized. The hydrophobic solvent may be one such solvent, or a mixture of two or more hydrophobic solvents.

The hydrophobic solvent desirably does not contain terpene or terpinols such as alpha-terpineol which forms a major constituent in pine oil type cleaning compositions as is known to the art.

The hydrophobic volatile solvent is one which is immiscible or which has only very limited solubility in water at room temperature (approx. 68° F., 20° C.) and desirably exhibits a solubility in water of not more than about 4.75 ml/100 ml at such temperatures. The hydrophobic solvent constituent should have a lower solubility in water than the hydrophilic solvent constituent discussed hereinafter. The hydrophobic solvents comprising Constituent A are present in a weight percentage of between 0.1–50.0% preferably 1–10% and most preferably between 2–3% with these weight percentages of constituent A based on the total weights of the concentrate compositions according to the invention.

As constituent (B) of the invention, there in included a hydrophilic solvent constituent which functions to stabilize and solubilize the hydrophobic volatile solvent of constituent (A) in the concentrate compositions. Hydrophilic solvents which find use in the present inventive compositions include certain lower alkyl alcohols such as methanol, ethanol, isopropanol, glycols, acetates, ether acetates and glycol ethers including propylene glycol methyl ether, dipropylene glycol methyl ether, tripropylene glycol methyl ether, propylene glycol n-propyl ether, ethylene glycol n-butyl ether, diethylene glycol n-butyl ether, diethylene glycol methyl ether, propylene glycol, ethylene glycol, and ethylene glycol monobutyl ether acetate. Others not particularly elucidated here, but which exhibit the functional characteristics described herein may also be used, and of course, two or more hydrophilic solvents may be used as a mixture.

The hydrophilic solvents comprising Constituent B of this invention should exhibit good solubility in water and exhibit solubility in water at room temperature (approx. 68° F., 20° C.) and desirably exhibit a solubility in water of at least about 5 ml hydrophilic solvent per 100 ml water, but most desirably are those which are considered to approach or demonstrate "infinite solubility". This hydrophilic solvent constituent preferably comprises between 0.1–50%, preferably 1–10% and most preferably between 4–6% with these weight percentages of constituent B based on the total weights of the concentrate compositions according to the invention.

By way of example, useful hydrophilic solvents including those recited above are presently commercially available under the tradenames DOWANOL (Dow Chemical Co., Midland Mich.) as well as CELLOSOLVE and CARBITOL (Union Carbide Co., Danbury Conn.). Further specific exemplary hydrophilic solvents are also indicated amongst the examples, below.

A further constituent (C) in the compositions of the invention is a nonionic surfactant compound having a hydrophile-lipophile balance ("HLB") value of at least about 10, and more preferably is one exhibiting a HLB value of between about 10 and about 20.

Particulary useful as constituent (C) are ethoxylated and/or propoxylated fatty alcohols which are the condensation products of a long chain ethylene oxide moiety and/or long chain propylene oxide moeity with an aliphatic alcohol preferably a primary or secondary aliphatic alcohol or alkyl phenol, preferably the primary or secondary alcohol contains 8 to 20 carbon atoms and the alkyl phenol-based moiety is one wherein the alkyl chain is straight or branched and contains 6 to 12 carbon atoms, preferably 6 to 9 carbon atoms.

Illustrative nonionic surfactants having the desired characteristics for formulation into the inventive compositions and which are available on the market under the tradenames of NEODOL and available from the Shell Chemical Company; those available under the tradename TERGITOL from the Union Carbide Company; those available under the tradename POLY-TERGENT from the Olin Chemical Co., as well as those available under the tradename PLURAFAC from BASF Inc. Specific examples include NEODOL 25-7 which is described to be a linear $C_{12}$–$C_{15}$ primary alcohol mixture condensed with 7 moles of ethylene oxide per mole of alcohol and exhibiting a HLB of 12.3; NEODOL 25-9 which is described to be a linear $C_{12}$–$C_{15}$ primary alcohol mixture condensed with 9 moles of ethylene oxide per mole of alcohol and exhibiting a HLB of 13.1; NEODOL 25-12 which is described to be a linear $C_{12}$–$C_{15}$ primary alcohol mixture condensed with 12 moles of ethylene oxide per mole of alcohol and exhibiting a HLB of 14.4; NEODOL 45-7 which is described to be a linear $C_{14}$–$C_{15}$ primary alcohol mixture condensed with 7 moles of ethylene oxide per mole of alcohol and exhibiting a HLB of 11.8; NEODOL 45-7T which is described to be a linear $C_{14}$–$C_{15}$ primary alcohol mixture condensed with 7 moles of ethylene oxide per mole of alcohol and exhibiting a HLB of 12.3; NEODOL 45-13 which is described to be a linear $C_{14}$–$C_{15}$ primary alcohol mixture condensed with 13 moles of ethylene oxide per mole of alcohol and exhibiting a HLB of 14.5; NEODOL 91-6 which is described to be a linear $C_9$–$C_{11}$ primary alcohol mixture condensed with 6 moles of ethylene oxide per mole of alcohol and exhibiting a HLB of 12.5; as well as NEODOL 91-8 which is described to be a linear $C_9$–$C_{11}$ primary alcohol mixture condensed with 8 moles of ethylene oxide per mole of alcohol and exhibiting a HLB of 13.9. Further specific examples include: TERGITOL 15-S-5 which is described to be a random secondary $C_{11}$–$C_{15}$ alcohol condensed with 5 moles of ethylene oxide per mole of alcohol and having an HLB of 10.5; TERGITOL 15-S-7 which is described to be a random secondary $C_{11}$–$C_{15}$ alcohol condensed with 7 moles of ethylene oxide per mole of alcohol and having an HLB of 12.1; TERGITOL 15-S-9 which is described to be a random secondary $C_{11}$–$C_{15}$ alcohol condensed with 9 moles of ethylene oxide per mole of alcohol and having an HLB of 13.3; TERGITOL 15-S-12 which is described to be a random secondary $C_{11}$–$C_{15}$ alcohol condensed with 12 moles of ethylene oxide per mole of alcohol and having an HLB of 14.5. Yet further examples include POLY-TERGENT SL-62 which exhibits an HLB of 14.0; POLY-TERGENT SL-92 which exhibits an HLB of 15.0, PLURAFAC D-25 which exhibits an HLB of 10.0 as well as PLURAFAC B-25-5 which exhibits an HLB or 12.0.

Also particularly useful as constituent (C) are nonionic surfactants which are block copolymers which may be described according to one of the the following formulae:

$(PO)_l(EO)_m(PO)_n$ $(EO)_l(PO)_m(EO)_n$ wherein the values of "l", "m" and "n" are desirably but not necessarily integer values selected to give a surfactant having exhibiting a HLB value of at least about 10, and more preferably is one exhibiting a HLB value of between about 10 and about 20. The groups EO and PO represent ethoxy, and propoxy groups respectively, and they may be present in any desired order in the chain. Specific examples of such a block copolymers include those which are presently commercially available in the PLURONIC and TETRONIC series of surfactants available from BASF Inc., those available in the MACOL series of surfactants from PPG.Mazer Chemical Co., as well as those available in the POLY-TERGENT E series of surfactants as well as the POLY-TERGENT P series of surfactants both available from the Olin Chemical Co.

Further examples of specific useful nonionic surfactants useful as constituent (C) which are presently commercially available are indicated in one or more of the examples, below.

The compositions of the invention include as constituent (D) a system which includes (D1) a nonionic fatty alcohol ethoxylate surfactant compound in conjunction with (D2) an alkoxylated alkanolamide.

Useful as constituent (D1) are nonionic fatty alcohol ethoxylated and/or propoxylated surfactant compounds may be the same materials which have been recited above with regard to constituent (C) but which differ in that those according to constituent (D1) may be characterized as having between about 1 and 3 moles of alkoxylation, particularly ethoxylation and/or propoxylation and an HLB value of between 7 and 9.

Constituent (D1) may be any of a number of known ethoxylated/propoxylated fatty alcohols which are the condensation products of a long chain ethylene oxide moiety and/or long chain propylene oxide moiety with an aliphatic alcohol preferably a primary or secondary aliphatic alcohol or alkyl phenol. Preferably the primary or secondary alcohol contains 8 to 20 carbon atoms and the alkyl phenol-based moiety is one wherein the alkyl chain is straight or branched and contains 6 to 12 carbon atoms, preferably 6 to 9 carbon atoms.

Illustrative nonionic surfactants useful as constituent (D1) having the desired characteristics for formulation are available on the market under the tradename of NEODOL products by Shell Chemical Company; TERGITOL products by Union Carbide Company. These include for example: NEODOL 23-3 which is described to be a linear $C_{12}$–$C_{13}$ primary alcohol mixture condensed with 3 moles of ethylene oxide per mole of alcohol and exhibiting a HLB of 7.9; NEODOL 25-3 which is described to be a linear $C_{12}$–$C_{15}$ primary alcohol mixture condensed with 3 moles of ethylene oxide per mole of alcohol and exhibiting a HLB of 7.8; as well as NEODOL 91-2.5 which is described to be a linear $C_9$–$C_{11}$ primary alcohol mixture condensed with 2.5 moles of ethylene oxide per mole of alcohol and exhibiting a HLB of 8.5. Further specific examples include: TERGITOL 15-S-3 which is described to be a random secondary $C_{11}$–$C_{15}$ alcohol condensed with 3 moles of ethylene oxide per mole of alcohol and having an HLB of 8.0, as well as TERGITOL NP-4 which is described to be an ethoxylated nonylphenol having an HLB of 8.9.

As has been recited above, constituent (D) further includes an alkoxylated alkanolamide which is particularly useful as constituent (D2). Such an alkoxylated alkanolamide includes $C_8$–$C_{24}$ alkyl di($C_2$–$C_3$ alkanol) amides, as represented by the following formula:

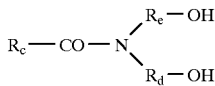

wherein $R_c$ is a branched or straight chain $C_8$–$C_{24}$ alkyl radical, preferably a $C_{10}$–$C_{16}$ alkyl radical and more preferably a $C_{12}$–$C_{14}$ alkyl radical, and $R_d$ and $R_e$ are a $C_1$–$C_4$ alkyl radical, preferably an ethyl radical; $R_d$ and $R_e$ may be the same or different.

Particularly useful alkanolamides useful as constituent (D2) include cocoamide diethanol amide, and soyamide diethanolamide.

The present inventors have found that the constituents forming (D1) and (D2) are desirably present in a weight ratio of (D1):(D2) of 1–10:1; more preferably are present in a weight ratio of about 3–5:1, more preferably are present in a weight ratio of about 4–5:1; and most preferably are present in a weight ratio of 4.2:1.

Overall, Constituent (D) is present in the inventive compositions to comprise between about 0.1 and 20% wt., more desirably Constituent (D) is present in amounts of between about 5 and 15% wt.

As constituent (E) of the invention, there is included a constituent which is effective in providing a germicidal effect. Exemplary materials which are useful as Constituent (E) include quaternary ammonium compounds and salts thereof include quaternary ammonium germicides which may be characterized by the general structural formula:

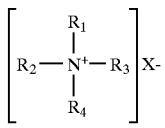

where at least one of $R_1$, $R_2$, $R_3$ and $R_4$ is a hydrophobic, aliphatic, aryl aliphatic or aliphatic aryl radical of from 6 to 26 carbon atoms, and the entire cation portion of the molecule preferably has a molecular weight of at least 165. The hydrophobic radicals may be long-chain alkyl, long-chain alkoxy aryl, long-chain alkyl aryl, halogen-substituted long-chain alkyl aryl, long-chain alkyl phenoxy alkyl, aryl alkyl, etc. The remaining radicals on the nitrogen atoms other than the hydrophobic radicals are substituents of a hydrocarbon structure usually containing a total of no more than 12 carbon atoms. The radicals $R_1$, $R_2$, $R_3$ and $R_4$ may be straight chained or may be branched, but are preferably straight chained, and may include one or more amide or ester linkages. The radical X may be any salt-forming counterion, especially a halogen such as chlorine or bromine.

Exemplary quaternary ammonium salts within the above description include the alkyl ammonium halides such as cetyl trimethyl ammonium bromide, alkyl aryl ammonium halides such as octadecyl dimethyl benzyl ammonium bromide, N-alkyl pyridinium halides such as N-cetyl pyridinium bromide, and the like. Other suitable types of quaternary ammonium salts include those in which the molecule contains either amide or ester linkages such as octyl phenoxy ethoxy ethyl dimethyl benzyl ammonium chloride, N-(laurylcocoaminoformylmethyl)-pyridinium chloride, and the like. Other very effective types of quaternary ammonium compounds which are useful as germicides include those in which the hydrophobic radical is characterized by a substituted aromatic nucleus as in the case of lauryloxyphenyltrimethyl ammonium chloride, cetylaminophenyltrimethyl ammonium methosulfate, dodecylphenyltrimethyl ammonium methosulfate, dodecylbenzyltrimethyl ammonium chloride, chlorinated dodecylbenzyltrimethyl ammonium chloride, and the like.

Preferred quaternary ammonium compounds which act as germicides and which are found useful in the practice of the present invention include those which have the structural formula:

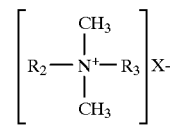

wherein $R_2$ and $R_3$ are the same or different $C_8$–$C_{12}$alkyl, or $R_2$ is $C_{12-16}$alkyl, $C_{8-18}$alkylethoxy, $C_{8-18}$alkylphenolethoxy and $R_3$ is benzyl, and X is a halide, for example chloride, bromide or iodide, or methosulfate. The alkyl groups recited in $R_2$ and $R_3$ may be straight chained or branched, but are preferably substantially linear.

Particularly useful quartenary germicides include compositions which include a single quartenary, as well as mixtures of two or more different quarternaries. Particularly useful quaternary germicides include BARDAC® 205M, and BARDAC® 208M, BTC® 885, and BTC® 888 which are described to be a blend of alkyl dimethyl benzyl ammonium chlorides; BARDAC® 2050, BARDAC® 2080 or BTC® 818 each of which is described to be based on dialkyl ($C_8$–$C_{10}$)dimethyl ammonium chloride; BARDAC® 2250, BARDAC® 2280 or BTC® 1010 each described to a composition which includes didecyl dimethyl ammonium chloride; BARDAC® LF and BARDAC® LF 80 each described to be based on dioctyl dimethyl ammonium chloride; BARQUAT® MB-50, HYAMINE® 3500, BARQUAT® MB-80, BTC® 835 or BTC 8358 each described to be based on alkyl dimethyl benzyl ammonium chloride; BARQUAT® MX-50, BARQUAT® MX-80, BTC® 824 or BTC® 8248 each described to be a composition based on alkyl dimethyl benzyl ammonium chloride; BARQUAT® OJ-50, BARQUAT® OJ-80, BTC® 2565, or BTC® 2658 each described to be a composition based on alkyl dimethyl benzyl ammonium chloride; BARQUAT® 4250, BARQUAT® 4280, BARQUAT® 4250Z, BARQUAT® 4280Z, BTC® 2125, or BTC® 2125M each described to be a composition based on alkyl dimethyl benzyl ammonium chloride and/or alkyl dimethyl ethyl benzyl ammonium chloride; BARQUAT® MS-100 or BTC® 324-P-100 each described to be based on myristyl dimethyl benzyl ammonium chloride; HYAMINE® 2389 described to be based on methyl dodecyl benzyl ammonium chloride and/or methyl dodecyl xylene-bis-trimethyl ammonium chloride; HYAMINE® 1622 described to be an aqueous solution of benzethonium chloride; HYAMINE® 3500-NF or BTC® 50 each described to be based on alkyl dimethyl benzyl ammonium chloride; as well as BARQUAT® 1552 or BTC® 776 described to be based on alkyl dimethyl benzyl ammonium chloride and/or dialkyl methyl benzyl ammonium chloride. (Each of these recited materials are presently commercially available from Lonza, Inc., Fairlawn, N.J. and/or from Stepan Co., Northfield Ill.). Mixtures of two or more of the above may also be used to form Constituent (E).

With regard to the effective amounts of Constituent (E), it may be present in any amount which imparts an effective germicidal effect when the concentrate composition is applied directly to a surface in need of disinfection, or when the concentrate composition if first diluted in a volume of water and this dilution is then applied to a surface in need of disinfection. Desirably, where a quaternary ammonium germicide of the type described above is used as constituent E, it is present so that when the concentrate composition is diluted in water, constituent E should be ultimately be present in an amount of from 100 to 2000 ppm (parts per million) but desirably at least about 200 ppm in such a dilution. Such an amount is generally effective in the sanitization of surfaces wherein a dilution is permitted a contact time of 10 minutes. Of course it is to be understood that greater dilutions may also be effective by permitting a longer contact time. With regard to the amounts of the quaternary ammonium germicide, such is desirably present between about 0.1–20% by weight based on the total weight of the concentrate composition, and preferably is present in amounts of from 4–6% by weight based on the total weight of the concentrate composition.

The concentrate compositions of the invention include a hydrotrope as constituent (F). Suitable hydrotropes include salts of aryl sulfonic acids such as naphthyl and benzene sulfonic acids, wherein the aromatic nucleus may be unsubstituted or substituted with lower alkyl groups, such as $C_{1-4}$ alkyl groups, especially methyl, ethyl and/or isopropyl groups. Up to three of such substitutents may be present in the aromatic nucleus, but preferably zero to two are preferred. The salt forming cation of the hydrotrope is preferably an alkali metal such as sodium or potassium, especially sodium. However, other water soluble cations such as ammonium, mono-, di- and tri- lower alkyl, i.e., $C_{1-4}$ alkanol ammonium groups can be used in the place of the alkali metal cations.

Exemplary hydrotropes include naphthalene sulfonates, benzene sulfonates, o-toluene sulfonates, m-toluene sulfonates, and p-toluene sulfonates; 2,3-xylene sulfonates, 2,4-xylene sulfonates, and 4,6-xylene sulfonates; cumene sulfonates, toluene sulfonates, wherein such exemplary hydrotropes are generally in a salt form thereof, including sodium and potassium salt forms. Further exemplary hydrotropes include lower alkyl sulfate salts, particularly those having from about one to six carbon atoms in the alkyl group. Preferably the hydrotropes are selected from sodium xylene sulfonate, sodium cumene sulfonate, and naphthalene sulfonate, and urea.

As is noted above, the compositions according to the invention are aqueous in nature. Water is added to the constituents in order to provide 100% by weight of the composition. The water may be tap water, but is preferably distilled and is most preferably deionized water. If the water is tap water, it is preferably substantially free of any undesirable impurities such as organics or inorganics, especially mineral salts which are present in hard water and which may thus interfere with the operation of any other constituents of the aqueous concentrate compositions according to the invention.

The compositions according to the invention may comprise one or more of the following optional components, the total weight of such optional constituents not exceeding about 20% by weight of the total weight of the composition, more preferably not exceeding about 10% by weight and most preferably being less than 10% by weight based on the total weight of the composition according to the invention.

For example, an optional, but in certain cases desirable constituent are fragrances, which may be derived from natural sources or synthetically produced. Such fragrances may be added in any conventional manner, admixing to a composition or blending with other constituents used to form a composition, in amounts which are found to be useful to enhance or impart the desired scent characteristic to the composition, and/or to cleaning compositions formed therefrom.

In compositions which include a fragrance, it is frequently desirable to include a fragrance solubilizer which assists in the dispersion, solution or mixing of the fragrance constituent in an aqueous base. These include known art compounds, including condensates of 2 to 30 moles of ethylene oxide with sorbitan mono- and tri-$C_{10}$–$C_{20}$ alkanoic acid esters having a HLB of at least about 8 to are also known as nonionic surfactants. Further examples of such suitable surfactants include water soluble nonionic surfactants of which many are commercially known and by way of non-limiting example include the primary aliphatic alcohol ethoxylates, secondary aliphatic alcohol ethoxylates, alkylphenol ethoxylates and ethylene-oxide-propylene oxide condensates on primary alkanols, and condensates of ethylene oxide with sorbitan fatty acid esters. This fragrance solubilizer component is added in minor amounts, particularly in amounts which are found effective in aiding in the solubilization of the fragrance component, but not in any significantly greater proportion, such that it would be considered as a detergent constituent. Such a minor amount recited herein is generally up to about 0.5% by weight of the total composition but is more generally an amount of about 0.1% by weight and less, and preferably is about 0.05% by weight and less.

Further optional, but advantageously included constituents are one or more coloring agents. Known coloring agents, may be incorporated in the compositions in any effective amount to improve or impart to the compositions a desired appearance or color. Such a coloring agent or coloring agents may be added in a conventional fashion, i.e., admixing to a composition or blending with other constituents used to form a composition.

One or more pH adjusting agents, including agents known to the art such as minor amounts of mineral acids, basic compositions, and organic acids may be used. An exemplary composition includes citric acid, such as is available in an anhydrous salt form of an alkali metal citric acid. The addition of an effective amount such a pH adjusting agent is useful in establishing a targeted pH range for compositions according to the invention.

An effective amount of a pH buffering composition so to maintain the pH of the inventive compositions may be included in the compositions. While the compositions of the invention generally do not require a pH buffering composition, the use of such a pH buffering composition may provide the benefit of hard water ion sequestration, should the inventive composition be diluted with further water by the consumer or other end user. Any pH buffering compound or pH buffer composition which is compatible with the aqueous compositions taught herein may be used, and many of these are well known to the art. Examples of such useful pH buffer compounds and/or pH buffering systems or compositions include the alkali metal phosphates, polyphospates, pyrophosphates, triphosphates, tetraphosphates, silicates, metasilicates, polysilicates, carbonates, hydroxides, and mixtures of the same. Certain salts, such as the alkaline earth phosphates, carbonates, hydroxides, can also function as buffers. It may also be suitable to use as buffers such materials as aluminosilicates (zeolites), borates, aluminates and certain organic materials such as gluconates, succinates, maleates, and their alkali metal salts. Also advantageously used are salts of ethylene-diaminetetraacetic acid, such as the mono-, di-, tri- and especially tetra-salts which may be formed with one or more salt forming anions particularly sodium. Such buffers keep the pH ranges of the compositions of the present invention within acceptable limits. Others, not particularly elucidated here may also be used. Preferably, citric acid, such as is available in an anhydrous salt form of an alkali metal citric acid is added as it is readily commercially available, and effective. The addition of such a buffering agent is desirable in certain cases wherein long term, i.e., prolonged storage, is to be anticipated for a composition, as well as insuring the safe handling of said aqueous composition.

A frequently desirable constituent in the concentrate compositions is an ingredient which improves the high temperature stability of the concentrate particularly when the concentrate is subjected to temperatures of greater than 120° F. (49° C.) for a period of at least 30 days. Exemplary materials include amines including 2-pyrrolidone and amine oxides. Further exemplary materials include high cloud point nonionic surfactants, i.e., those which exhibit cloud points in water at temperatures greater than 48° C. A further and particularly preferred material is urea.

One general class of useful amine oxides which are also known as specific types of nonionic surfactant compounds include alkyl di(lower alkyl) amine oxides in which the alkyl group has about 10–20, and preferably 12–16 carbon atoms, and can be straight or branched chain, saturated or unsaturated. The lower alkyl groups include between 1 and 7 carbon atoms. Examples include lauryl dimethyl amine oxide, myristyl dimethyl amine oxide, and those in which the alkyl group is a mixture of different chain lengths, dimethyl cocoamine oxide, dimethyl (hydrogenated tallow) amine oxide, and myristyl/palmityl dimethyl amine oxide.

A further class of useful amine oxides include alkyl di (hydroxy lower alkyl) amine oxides in which the alkyl group has about 10–20, and preferably 12–16 carbon atoms, and can be straight or branched chain, saturated or unsaturated. Examples are bis(2-hydroxyethyl) cocoamine oxide, bis(2-hydroxyethyl) tallowamine oxide; and bis(2-hydroxyethyl) stearylamine oxide.

Further useful amine oxides include those which may be characterized as alkylamidopropyl di(lower alkyl) amine oxides in which the alkyl group has about 10–20, and preferably 12–16 carbon atoms, and can be straight or branched chain, saturated or unsaturated. Examples are cocoamidopropyl dimethyl amine oxide and tallowamidopropyl dimethyl amine oxide; and Additional useful amine oxides include those which may be referred to as alkylmorpholine oxides in which the alkyl group has about 10–20, and preferably 12–16 carbon atoms, and can be straight or branched chain, saturated or unsaturated. Most preferably the amine oxide is myristamine oxide.

Further examples of such useful include nonionic surfactant compositions based on amine oxides include those which are presently commercially available and include those under the trade name AMMONYX from Stepan Co. (Northfield, Ill.).

A further and particularly preferred material which improves the high temperature stability of the concentrate is urea. The present inventors have observed that this material is effective providing desirably high temperature stability characteristics to the concentrate compositions and is widely commercially available at low cost.

Preservatives may also be added in minor amounts in the formulations according to the invention, of which known art compositions may be used. Examples of such preservatives compounds include those which are presently commercially available under the tradenames Kathon® CG/ICP (Rohm & Haas, Philadelphia Pa.), Suttocide® A (Sutton Labs, Chatham N.J.) as well as Midtect® TFP (Tri-K Co., Emerson, N.J.). Such preservative compositions are generally added in only minor amounts, i.e., amounts of about 0.5% by weight of the total composition, more generally an amount of about 0.1% by weight and less, and preferably are included in amounts of about 0.05% by weight and less. However as the concentrate compositions according to the invention are primarily sanitizing compositions the use of a preservative is generally not required.

Thickening and/or gelling agents may be added to the hard surface cleaning compositions according to the present invention in order to modify the viscous and/or thixatropic properties thereof. For example, in certain applications it is contemplated that it may be desirable to provide a more viscous compositions, viz., higher viscosities than that of water, whether for esthetic or functional reasons. For example, the addition of a suitable amount of a gelling agent may be desired not only for aesthetic reasons but also to limit the spreading of the composition as it is applied to a surface. This function is desirable in providing a means to apply the composition over a limited area, such as directly onto a stain, without applying an excess onto the surrounding area of a surface. This function also aids in the surface retention time on non-horizontal surface, ensuring that the cleaning composition is in contact with a stained surface without flowing off too rapidly. Similarly, thixatropic properties may also be desired under certain circumstances. In order to provide such functional features to the composition, known thickening and gelling agents including, but not limited to, cellulose compounds, xanthan gums, polymers and/or clays may be added.

Other conventional optional additives, although not particularly elucidated above may also be included in the present inventive compositions.

The concentrate compositions according to the invention are normally expected to be be diluted in order to form a disinfecting composition therefrom. Such disinfecting compositions may be easily prepared by diluting measured amounts of the concentrate compositions in further amounts of water by the consumer or other end user in certain weight ratios of concentrate composition:water, and optionally, agitating the same to ensure even distribution of the composition in the water. These dilutions may be either as weight or volume ratio proportions. Useful dilutions may vary over a wide range for example from ratios of concentrate composition:water of 1:0, to extremely dilute dilutions such as 1:10,000. Desirably, for most sanitizing purposes dilutions of concentrate composition:water are preferably of from 1:10–1:100, and desirably are intended to be diluted in a composition:water dilution ratio range of 1:64–102. The actual dilution selected is in part determinable by the rate of sanitization which is to be imparted to a surface(s), with lower dilutions of composition concentrate:water and longer contact times of disinfecting compositions being more efficacious in providing a sanitizing effect. It is nonetheless to be understood that the aqueous concentrate compositions according to the invention may be used without further dilution, and may be used "as is" without a further aqueous dilution.

In accordance with preferred embodiments of the invention, when a quantity of the concentrate compositions taught herein are added to a larger volume of water, a blooming characteristic is manifested. Such "blooming" may be broadly characterized as the formation of milky, creamy or cloudy appearance which is manifested when a dilutable composition is added to a larger volume or quantity of water. Such "blooming" may be alternately characterized as the reduction of transmitted light through an amount of water by at least 30%, desirably by at least 40%, yet more desirably by at least about 50%, and yet most desirably by at least 60% or more when a dilution of the concentrate composition:water with the weight or volume ratio range of from 1:64–102 is formed. That such blooming may be attained without the use of pine oil fractions as is common in certain commercially available pine oil containing preparations is surprising.

The compositions according to the invention exhibit san-titizing properties, and are useful in the sanitization of surfaces wherein the presence of various viruses, molds, fungi, bacteria, and mildew are suspected.

In preferred embodiments, aqueous dilutions of the concentrated aqueous liquid disinfectant compositions exhibit antimicrobial efficacy against at least one of the following bacteria: *Staphylococcus aureus, Salmonella choleraesuis, Pseudomonas aeruginosa,* where the ratio of concentrate composition:water is 1:64 to 1:102. According to more preferred embodiments, aqueous dilutions of the concentrated aqueous liquid disinfectant compositions exhibit antimicrobial efficacy against at least two of the following bacteria: *Staphylococcus aureus, Salmonella choleraesuis, Pseudomonas aeruginosa,* where the ratio of concentrate composition:water of 1:64 to 1:102. Such aqueous dilutions may be classified as "broad spectrum disinfectant" compositions. According to a still more preferred embodiment, aqueous dilutions of the concentrated aqueous liquid disinfectant compositions exhibit antimicrobial efficacy against all three of the following bacteria: *Staphylococcus aureus, Salmonella choleraesuis, Pseudomonas aeruginosa,* where the ratio of concentrate composition:water of 1:64 to 1:102. Such aqueous dilutions may be classified as "hospital strength disinfectant" compositions. In each of these respective preferred, more preferred and still more preferred embodiments described immediately above, those which exhibit antimicrobial efficacy at greater aqueous dilutions of the concentrated aqueous liquid disinfectant compositions in water, such as at concentrate:water dilution ratios ratios of 1:102, are preferred over concentrate:water dilution ratios of 1:85, and still more preferred over concentrate:water dilution ratios of 1:64.

Such dilution ratios of concentrate:water as described above may be volume/volume basis, or a weight/weight basis.

The following examples below illustrate exemplary and among them preferred formulations of the composition according to the instant invention. It is to be understood that these examples are presented by means of illustration only and that further useful formulations fall within the scope of this invention and the claims may be readily produced by one skilled in the art and not deviate from the scope and spirit of the invention.

EXAMPLES

Exemplary formulations illustrating certain preferred embodiments of the inventive compositions and described in more detail in Table 1 below were formulated generally in accordance with the following protocol.

Into a suitably sized vessel, a measured amount of water was provided after which the constituents were added in the following sequence: surfactants and solvents, and lastly the fragrance constituents. All of the constituents were supplied at room temperature, except for the linear alcohol ethoxylate which was first gently heated and melted. Mixing of the constituents was achieved by the use of a mechanical stirrer with a small diameter propeller at the end of its rotating shaft. Mixing, which generally lasted from 5 minutes to 120 minutes was maintained until the particular exemplary formulation appeared to be homogeneous.

It is to be noted that the constituents might be added in any order, but it is preferred that water be the initial constituent provided to a mixing vessel or apparatus as it is the major constituent and addition of the further constituents thereto is convenient.

The exact compositions of the example formulations are listed on Table 1; the weights given are the "as is" weight of materials as supplied by their respective producer.

TABLE 1

| Constituents | Ex.1 | Ex.2 | Ex.3 | Ex.4 | Ex.5 | Ex.6 | Ex.7 | Ex.8 | Ex.9 | Ex.10 |
| --- | --- | --- | --- | --- | --- | --- | --- | --- | --- | --- |
| odorless mineral spirits | 3.00 | 3.00 | 3.00 | 3.00 | 2.40 | 2.40 | 3.00 | 2.60 | 2.60 | 2.60 |
| hydrocarbon mixture | — | — | — | — | — | — | — | — | — | — |
| diethylene glycol monobutyl ether | 7.50 | 7.50 | 7.50 | 7.50 | 4.00 | 4.80 | 4.50 | 4.50 | 4.50 | 5.10 |
| $C_{14}$–$C_{15}$ linear primary alcohol (7 mol) ethoxylate | 3.00 | 3.00 | 3.00 | 6.60 | 2.40 | 4.10 | — | 4.50 | 4.50 | 4.50 |
| $C_9$–$C_{11}$ linear primary alcohol (2.5 mol) ethoxylate | — | — | — | — | — | — | — | — | — | — |
| myristamine oxide (30%) | — | — | — | — | — | 4.80 | — | — | — | — |
| poly(ethoxylpropoxy)-monohexyl ether; monooctyl ether; monodecyl ether | — | — | — | — | — | — | 3.90 | — | — | — |
| urea | — | — | — | — | — | — | — | 4.00 | 6.00 | 6.00 |
| 2-pyrrolidone | — | — | — | — | 5.60 | — | — | — | — | — |
| $C_9$–$C_{11}$ linear primary alcohol (2.5 mol) ethoxylate | 8.40 | 8.40 | 8.40 | 8.40 | 6.72 | 6.72 | 8.40 | 7.40 | 7.40 | 7.40 |
| soyamide DEA | 2.00 | 2.00 | 2.00 | 2.00 | 1.60 | 1.60 | 2.00 | 1.75 | 1.75 | 1.75 |
| alkyl dimethyl benzyl ammonium chloride (80%) | 6.40 | 6.40 | 5.15 | 6.40 | 6.40 | 6.40 | 6.60 | 660 | 6.60 | 5.30 |
| mixture of alkyl dimethyl benzyl ammonium chloride, octyl-decyl-, dioctyl- and didecyl- dimethyl ammonium chlorides (80%) | — | — | — | — | — | — | — | — | — | — |
| Barquat MX-50 (50%) | — | — | — | — | — | — | — | — | — | 2.10 |
| Bardac LF (50%) | | | | | | | | | | |

TABLE 1-continued

| Constituents | | | | | | | | | | |
|---|---|---|---|---|---|---|---|---|---|---|
| sodium xylene sulfonate (40%) | 2.50 | 2.50 | 2.50 | 2.50 | 2.00 | 2.00 | 1.85 | 1.25 | 1.25 | 1.25 |
| $Na_4EDTA$ (38%) | 1.40 | 3.60 | 3.60 | 3.60 | 3.60 | 3.60 | 3.60 | 3.60 | 3.60 | 3.60 |
| sodium citrate dihydrate | — | — | — | — | — | — | — | — | — | — |
| fragrance | — | — | — | — | — | — | — | — | — | — |
| coloring agent | — | — | — | — | — | — | — | — | — | — |
| deionized water | 65.80 | 63.60 | 64.85 | 60.00 | 65.28 | 63.58 | 66.15 | 63.80 | 61.80 | 59.90 |

| Constituents | Ex.11 | Ex.12 | Ex.13 | Ex.14 | Ex.15* | Ex.16 |
|---|---|---|---|---|---|---|
| odorless mineral spirits | 2.60 | 2.40 | 2.60 | 2.60 | 1.30 | 2.40 |
| hydrocarbon mixture | — | 0.20 | — | — | — | 0.20 |
| diethylene glycol monobutyl ether | 5.10 | 6.00 | 6.00 | 6.00 | 6.00 | 6.00 |
| $C_{14}$–$C_{15}$ linear primary alcohol (7 mol) ethoxylate | 4.50 | 6.70 | 6.70 | 6.70 | 6.70 | 6.70 |
| $C_9$–$C_{11}$ linear primary alcohol (2.5 mol) ethoxylate | — | 7.00 | 7.00 | 7.00 | 7.00 | 7.00 |
| myristamine oxide (30%) | — | — | — | — | — | — |
| poly(ethoxyl propoxy)-monohexyl ether; monooctyl ether; monodecyl ether | — | — | — | — | — | — |
| urea | 6.00 | 6.50 | 6.50 | 6.50 | 6.50 | 6.50 |
| 2-pyrrolidone | — | — | — | — | — | — |
| $C_9$–$C_{11}$ linear primary alcohol (2.5 mol) ethoxylate | 7.40 | — | — | — | — | — |
| soyamide DEA | 1.75 | 1.65 | 1.65 | 1.65 | 1.65 | 1.65 |
| alkyl dimethyl benzyl ammonium chloride (80%) | 5.28 | — | — | — | — | — |
| mixture of alkyl dimethyl benzyl ammonium chloride, octyl-decyl-, dioctyl- and didecyl- dimethyl ammonium chlorides (80%) | — | 6.40 | 6.40 | 6.40 | 6.40 | 6.40 |
| Barquat MX-50 (50%) | — | — | — | — | — | — |
| Bardac LF (50%) | 2.11 | — | — | — | — | — |
| sodium xylene sulfonate (40%) | 1.25 | 1.00 | 1.00 | 1.00 | 1.00 | 1.00 |
| $Na_4EDTA$ (38%) | 3.60 | — | 3.60 | — | — | — |
| sodium citrate dihydrate | — | 1.10 | — | 1.10 | 1.10 | 1.10 |
| fragrance | 0.50 | 1.0 | 0.50 | 0.50 | 0.50 | 0.50 |
| coloring agent | — | — | 0.004 | 0.004 | 0.001 | 0.001 |
| deionized water | 59.91 | 60.05 | 58.05 | 60.55 | 60.35 | 60.55 |

*the formulation according to Ex. 15 additionally included 1.30% wt. of kerosene Table 1 illustrates the actual weight of the indicated material added to form a respective exemplary formulation. The identity of the constituents used to form the example formulations, and where relevant the weight percent of the actives in a respective material used, are specifically identified on Table 2 following. Thus, an amount of a material indicated on Table 1 should be multiplied by the % wt of active which it contains to achieve the amount of a particular compound in a respective formulation. Where no weight percentage is indicated, such indicates a "100% wt. active" constituent.

TABLE 2

| | |
|---|---|
| odorless mineral spirits | Shell Odorless Mineral Spirits (Shell Chemical Co., Houston TX) |
| diethylene glycol monobutyl ether | DOWANOL DB, 100% wt. (Dow Chemical Co., Midland MI) |
| $C_{14}$–$C_{15}$ linear primary alcohol (7 mol) ethoxylate | NEODOL 45-7, 100% wt. (Shell Chemical Co., Houston TX) |
| $C_9$–$C_{11}$ linear primary alcohol (2.5 mol) ethoxylate | NEODOL 91-2.5, 100% wt. (Shell Chemical Co., Houston TX) |
| myristamine oxide (30%) | AMMONYX MO, 30% wt. (Stepan Co., Northfield IL) |
| poly(ethoxy/propoxy)-monohexyl ether; monooctyl ether; monodecyl ether | POLYTERGENT SL-92, 100% wt. (Olin Corp., Stamford, CT) |
| urea | urea, commercial grade (Borden Chem. Co.) |
| 2-pyrrolidone | 2-pyrrolidone (BASF Inc., Mt. Olive, NJ) |
| $C_9$–$C_{11}$ linear primary alcohol (2.5 mol) ethoxylate | NEODOL 91-2.5, 100% wt. (Shell Chemical Co., Houston TX) |
| soyamide DEA | ALKAMIDE DIN-295/S, 100% wt. (Rhone-Poulenc Surfactant & Specialty Chem. Div, Cherry Hill, NJ) |
| alkyl dimethyl benzyl ammonium chloride (80% wt.) | BTC-8358, 80% wt., (Stepan Co., Northfield IL) |
| alkyl dimethylbenzyl ammonium chloride (50% wt. actives) | Barquat MX-50 (50%) (Lonza Inc., Fairlawn NJ) |
| dioctyl dimethyl ammonium chloride (50% wt. actives) | Bardac LF (50%) (Lonza Inc., Fairlawn NJ) |
| mixture of alkyl dimethyl benzyl ammonium chloride, octyl-decyl-, dioctyl- and didecyl- dimethyl ammonium chlorides (80%) | BTC-888, 80% wt., (Stepan Co., Northfield IL) |
| sodium xylene sulfonate (40%) | STEPANATE SXS 40% wt., (Stepan Co., Northfield IL) |
| $Na_4EDTA$ (38%) | VERSENE 100 38% wt., (Dow Chemical Co., Midland MI) |
| sodium citrate dihydrate | sodium citrate dihydrate, anhydrous (Archer Daniels Midland) |
| fragrances and colorants | aqueous dispersible, proprietary compositions |
| deionized water | deionized water |

In order to evaluate the blooming characteristics of the exemplary formulations, dilutions of an individual formuation were produced by adding 1 part formulation to 100 parts of tap water in a clear glass beaker. Immediately subsequent to the addition of the formulation to the water, the contents of the beaker were stirred for several seconds to ensure good mixing. Thereafter, using a Sybron/Brinkman PC 801 Colorimeter apparatus the light transmittance measured at 620 nanometers was evaluated for each sample, and reported as a percentage of transmittance based on a control formulation (tap water) which was assigned a light transmittance percentage of "100%." These results are reported on Table 3.

TABLE 3

| formulation | % transmittance |
|---|---|
| control (water) | 100 |
| 1 part (Ex. 1):100 parts (water) | 19.0 |
| 1 part (Ex. 2):100 parts (water) | 14.9 |
| 1 part (Ex. 3):100 parts (water) | 23.1 |
| 1 part (Ex. 4):100 parts (water) | 30.0 |
| 1 part (Ex. 5):100 parts (water) | 20.0 |
| 1 part (Ex. 6):100 parts (water) | 25.7 |
| 1 part (Ex. 7):100 parts (water) | 25.3 |
| 1 part (Ex. 8):100 parts (water) | 25.8 |
| 1 part (Ex. 9):100 parts (water) | 32.2 |
| 1 part (Ex. 10):100 parts (water) | 21.5 |
| 1 part (Ex. 11):100 parts (water) | 16.0 |
| 1 part (Ex. 13):100 parts (water) | 17.3 |
| 1 part (Ex. 14):100 parts (water) | 18.1 |
| 1 part (Ex. 15):100 parts (water) | 14.9 |
| 1 part (Ex. 16):100 parts (water) | 13.2 |

Note:
Transmittance measured at 620 nm where tap water gives a % transmittance of 100.

As may be seen from the reported results, each of the formulations according to Table 1 evinced a significant blooming behavior when diluted into a larger volume of water.

Evaluation of Antimicrobial Efficacy

Several of the exemplary formulations described in more detail on Table 1 above were evaluated in order to evaluate their antimicrobial efficacy against *Staphylococcus aureus* (gram positive type pathogenic bacteria) (ATCC 6538), *Salmonella choleraesuis* (gram negative type pathogenic bacteria) (ATCC 10708), and *Pseudomonas aeruginosa* (ATCC 15442). The testing was performed generally in accordance with the protocols outlined in "Use-Dilution Method", Protocols 955.14, 955.15 and 964.02 described in Chapter 6 of "Official Methods of Analysis", 16$^{th}$ Edition, of the Association of Official Analytical Chemists; "Germicidal and Detergent Sanitizing Action of Disinfectants", 960.09 described in Chapter 6 of "Official Methods of Analysis", 15$^{th}$ Edition, of the Association of Official Analytical Chemists; or American Society for Testing and Materials (ASTM) E 1054-91 the contents of which are herein incorporated by reference. This test is also commonly referred to as the "AOAC Use-Dilution Test Method".

As is appreciated by the skilled practitioner in the art, the results of the AOAC Use-Dilution Test Method indicate the number of test substrates wherein the tested organism remains viable after contact for 10 minutes with at test disinfecting composition/total number of tested substrates (cylinders) evaluated in accordance with the AOAC Use-Dilution Test. Thus, a result of "0/60" indicates that of 60 test substrates bearing the test organism and contacted for 10 minutes in a test disinfecting composition, 0 test substrates had viable (live) test organisms at the conclusion of the test. Such a result is excellent, illustrating the excellent disinfecting efficacy of the tested composition. A result of "1/60" indicates that of 60 test substrates bearing the test organism and contacted for 10 minutes in a test disinfecting composition, 1 test substrate had viable (live) test organisms at the conclusion of the test. One positive tube in 60 (ie. 1/60) is allowable in order to satisfy current US EPA registration requirements.

Various formulations according to the Examples illustrated on Table 1 were either evaluated using a full 60 test substrates which is sufficient to satisfy the current requirements for US EPA registration, or were only initially screened using a smaller sampling of 30 test substrates. In either instance, the AOAC Use-Dilution Test Method was generally followed. A result of "0/30" provides an indicator of excellent disinfecting efficacy, and suggest a high probability that the tested formulation would satisfy current US EPA registration requirements if tested using 60 test substrates.

Results of the antimicrobial testing are indicated on Table 4, below at volume ratios of a concentrate composition according to Table 1 in water of 1:102, unless otherwise indicated as being at 1:85 or 1:64. The reported results indicate the number of test cylinders with live test organisms/number of test cylinders tested for each example formulation and organism tested.

TABLE 4

| | Ex.1 | Ex.2 | Ex.3 | Ex.4 | Ex.5 | Ex.6 | Ex.7 | Ex.8 | Ex.9 | Ex.10 | Ex.11 | Ex.13 | Ex.15 |
|---|---|---|---|---|---|---|---|---|---|---|---|---|---|
| *Staphylococcus aureus* | 0/60 | 0/60 | 0/30 | 0/30 | 0/30 | 1/60 | 0/60 | 0/60 | 0/60 | 0/30 | 0/60 | 0/60 | 0/60 |
| *Salmonella choleraesuis* | 0/60 | 0/60 | 0/30 | 0/30 | 0/30 | 0/60 | 0/60 | 0/60 | 0/60 | 0/30 | 0/60 | 1/60 | 0/60 |
| *Pseudomonas aeruginosa* | 0/60 | 0/60 | 0/30 | 2/30 | 0/30 | — | 1/60 | 3/60 | 5/60 | — | 1/60 | 0/60 | 0/60 |
| *Pseudomonas aeruginosa* | 1/60* | — | — | 0/30* | — | — | — | 0/60* | 0/60* | — | — | — | — |

"—"indicates not tested
*indicates dilution ratios of concentrate:water of 1:64
+indicates dilution ratios of concentrate:water of 1:85
All other samples at dilution ratios of concentrate:water of 1:102

As may be seen from the results indicated above, the compositions according to the invention provide excellent antimicrobial efficacy against known bacteria commonly found in bathroom, kitchen and other environments. Such advantages clearly illustrate the superior characteristics of the compositions, the cleaning and antimicrobial benefits attending their use which were not before known to the art.

The efficacy of the formulations according to Examples 1–11 as described in Table 4 above is identified in Table 5 below with regard to their appropriate categorization as "hospital strength" or "broad spectrum" type disinfecting compositions. In Table 5, "b.s." indicates that at the specified concentrate:water dilution the said aqueous dilution may be categorized as a "broad spectrum" disinfecting composition as it exhibits antimicrobial efficacy against at least two of the bacteria selected from *Staphylococcus aureus, Salmonella choleraesuis,* and *Pseudomonas aeruginosa* in accordance with the AOAC Use-dilution Test method outlined above. The legend "h.s." indicates that at the specified concentrate:water dilution the said aqueous dilution may be categorized as a "hospital strength" type disinfecting composition as it exhibits antimicrobial efficacy against all three of the bacteria: *Staphylococcus aureus, Salmonella choleraesuis,* and

TABLE 5

| | dilution ratio of concentrate:water | | |
|---|---|---|---|
| | 1:64 | 1:85 | 1:102 |
| Ex. 1 | h.s. | — | b.s. |
| Ex. 2 | — | — | h.s. |
| Ex. 3 | — | — | h.s. |
| Ex. 4 | h.s. | — | b.s. |
| Ex. 5 | — | — | h.s. |
| Ex. 6 | — | — | b.s. |
| Ex. 7 | — | — | h.s. |
| Ex. 8 | — | h.s. | b.s. |
| Ex. 9 | — | h.s. | b.s. |
| Ex. 10 | — | — | b.s. |
| Ex. 11 | — | — | b.s. |
| Ex. 13 | — | — | b.s. |
| Ex. 16 | — | — | b.s. |

"—" indicates not tested

It is to be noted that where an aqueous dilution described in Tables 4 and 5 may be categorized as a "hospital strength" type disinfecting compositions, it inherently is categorized as a "broad spectrum" type disinfecting composition as well. Further it is to be noted that where an aqueous dilution described in Tables 4 and 5 may be categorized as a "hospital strength" type disinfecting composition at a higher dilution of concentrate composition in water, such as concentrate-:water ratios of 1:102, it may also be inherently categorized as exhibiting "hospital strength" type disinfecting composition at a relatively lesser dilution of concentrate composition in water, such as concentrate:water ratios of 1:85 and 1:64.

It is to be noted that concentrate:water dilution ratios of 1:102 corresponds to a dilution of 1.25 fl.oz. concentrate per 1 gallon of water (36.8 ml per 3.785 liters); dilution ratios of 1:85 corresponds to a dilution of 1.50 fl.oz. concentrate per 1 gallon of water (44.35 ml per 3.785 liters); dilution ratios of 1:64 corresponds to a dilution of 2.0 fl.oz. concentrate per 1 gallon of water (59.1 ml per 3.785 liters).

While described in terms of the presently preferred embodiments, it is to be understood that the present disclosure is to be intereprected as by way of illustration, and not by way of limitation, and that various modifications and alterations apparent to one skilled in the art may be made without departing from the scope and spirit of the present invention.

We claim:

1. An aqueous liquid disinfectant concentrate composition which comprises:
    (A) 0.1 to 50 wt. % of a volatile hydrophobic solvent;
    (B) 0.1 to 50 wt. % of a hydrophilic solvent which stabilizes the volatile hydrophobic solvent;
    (C) a nonionic alkoxylated fatty alcohol surfactant having a HLB value of between about 10 and about 15.
    (D) 0.1 to 20 wt. % of a combination of (D1) a fatty alcohol ethoxylate or propxylate having 2–3 moles ethoxylation and/or propoxylation and an HLB value of between 7 and 9, with, (D2) an alkanolamide wherein the weight ratio of (D1):(D2) is 10.0–1.0:1.
    (E) 0.1 to 20 wt. % of a non-phenolic compound which is effective in providing a germicidal effect;
    (F) hydrotrope; and,
    (G) water.

2. The aqueous liquid disinfectant concentrate composition according to claim 1 wherein:
    the weight ratio of (D1):(D2) is 3–5:1.

3. The aqueous liquid disinfectant concentrate composition according to claim 1 wherein:
    the volatile hydrophobic solvent (A) is selected from the group consisting of mineral spirits, $C_6$–$C_{12}$ alkanes, and $C_6$–$C_{12}$ alkenes.

4. The aqueous liquid disinfectant concentrate composition according to claim 1 wherein:
    the hydrophilic solvent (B) is selected from the group consisting of lower alkyl alcohols, glycols, acetates, ether acetates and glycol ethers.

5. The aqueous liquid disinfectant concentrate composition according to claim 1 wherein:
    the hydrophilic solvent (B) is selected from the group consisting of: methanol, ethanol, isopropanol, propylene glycol methyl ether, dipropylene glycol methyl ether, tripropylene glycol methyl ether, propylene glycol n-propyl ether, ethylene glycol n-butyl ether, diethylene glycol n-butyl ether, diethylene glycol methyl ether, propylene glycol, ethylene glycol, and ethylene glycol monobutyl ether acetate.

6. The aqueous liquid disinfectant concentrate composition according to claim 1 wherein:
    the hydrophilic solvent (B) exhibits a solubility in water of at least about 5 ml of the said hydrophilic solvent per 100 ml of water.

7. The aqueous liquid disinfectant concentrate composition according to claim 1 wherein the nonionic surfactant (C) is one or more condensation products of a long chain ethylene oxide moiety and/or long chain propylene oxide moeity with an aliphatic primary or secondary alcohol.

8. The aqueous liquid disinfectant concentrate composition according to claim 1 wherein the nonionic surfactant (C) is one or more condensation products of a long chain ethylene oxide moiety and/or long chain propylene oxide moeity with an alkyl phenol-based moiety wherein the alkyl chain is straight or branched and contains 6 to 12 carbon atoms.

9. The aqueous liquid disinfectant concentrate composition according to claim 1 wherein the nonionic surfactant (C) is one or more block copolymers according to one of the formulae:

$(PO)_l(EO)_m(PO)_n$ $(EO)_l(PO)_m(EO)_n$ where:
    l, m and n are integer values selected so that the resulting block copolymer surfactant exhibits an HLB value of at least about 10;
    EO represents an ethoxy group; and,
    PO represents a propoxy group.

10. The aqueous liquid disinfectant concentrate composition according to claim 1 wherein the fatty alcohol ethoxylate or propxylate having 2–3 moles ethoxylation and/or propoxylation and an HLB value of between 7 and 9 (D1) is one or more condensation products of a long chain ethylene oxide moiety and/or long chain propylene oxide moiety with an primary or secondary aliphatic alcohol containing 8 to 20 carbon atoms.

11. The aqueous liquid disinfectant concentrate composition according to claim 1 wherein the fatty alcohol ethoxylate or propxylate having 2–3 moles ethoxylation and/or propoxylation and an HLB value of between 7 and 9 (D1) is one or more condensation products of a long chain ethylene oxide moiety and/or long chain propylene oxide moiety with an alkyl phenol-based moiety wherein the alkyl chain is straight or branched and contains 6 to 12 carbon atoms.

12. The aqueous liquid disinfectant concentrate composition according to claim 1 wherein the (D2) alkanolamide is a $C_8$–$C_{24}$ alkyl di($C_2$–$C_3$ alkanol) amides as represented by the formula:

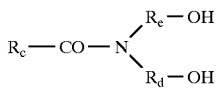

wherein $R_c$ is a branched or straight chain $C_8$–$C_{24}$ alkyl radical,
$R_d$ and $R_e$ are each a $C_1$–$C_4$ alkyl radical.

13. The aqueous liquid disinfectant concentrate composition according to claim 1 wherein the (D2) alkanolamide is cocoamide diethanol amide or soyamide diethanolamide.

14. The aqueous liquid disinfectant concentrate composition according to claim 1 wherein the non-phenolic compound which is effective in providing a germicidal effect (E) is a quaternary ammonium germicide according to the structural formula:

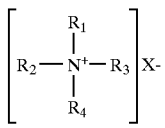

where at least one of $R_1$, $R_2$, $R_3$ and $R_4$ is a hydrophobic, aliphatic, aryl aliphatic or aliphatic aryl radical of from 6 to 26 carbon atoms and the remaining radical(s) $R_1$, $R_2$, $R_3$ and/or $R_4$ is/are substituent of hydrocarbon structure containing a total of no more than 12 carbons, and the entire cation portion of the molecule has a molecular weight of at least 165, and X may be any salt-forming anionic radical.

15. The aqueous liquid disinfectant concentrate composition according to claim 1 wherein the non-phenolic compound which is effective in providing a germicidal effect (E) is a quarternary ammonium compounds according to the structural formula:

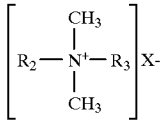

wherein $R_2$ and $R_3$ are the same or different $C_8$–$C_{12}$alkyl, or $R_2$ is $C_{12-16}$alkyl, $C_{8-18}$alkylethoxy, $C_{8-18}$alkylphenolethoxy and $R_3$ is benzyl, and X is a halide or methosulfate.

16. The aqueous liquid disinfectant concentrate composition according to claim 1 wherein the non-phenolic compound which is effective in providing a germicidal effect (E) is selected from the group consisting of: blends of alkyl dimethyl benzyl ammonium chlorides, dialkyl($C_8$–$C_{10}$) dimethyl ammonium chloride, didecyl dimethyl ammonium chloride, dioctyl dimethyl ammonium chloride, alkyl dimethyl benzyl ammonium chloride, alkyl dimethyl benzyl ammonium chloride, alkyl dimethyl benzyl ammonium chloride and/or alkyl dimethyl ethyl benzyl ammonium chloride, myristyl dimethyl benzyl ammonium chloride, methyl dodecyl benzyl ammonium chloride and/or methyl dodecyl xylene-bix-trimethyl ammonium chloride, benzethonium chloride, alkyl dimethyl benzyl ammonium chloride, dialkyl methyl benzyl ammonium chloride and mixtures thereof.

17. The aqueous liquid disinfectant concentrate composition according to claim 1 wherein composition includes a constituent which improves the high temperature stability of the concentrate.

18. The aqueous liquid disinfectant concentrate composition according to claim 17 wherein said constituent which improves the high temperature stability of the concentrate is an amine, amine oxide, a nonionic surfactant which exhibits a cloud point in water at temperatures greater than 48° C., or urea.

19. The aqueous liquid disinfectant concentrate composition according to claim 18 wherein the amine oxide is an alkyl di(lower alkyl) amine oxide in which the alkyl group has about 10–20 carbon atoms, which may be straight chained or branched chained, saturated or unsaturated, and where the lower alkyl groups include between 1 and 7 carbon atoms.

20. The aqueous liquid disinfectant concentrate composition according to claim 19 wherein said alkyl di(lower alkyl) amine oxide is selected from the group consisting of lauryl dimethyl amine oxide, myristyl dimethyl amine oxide, dimethyl cocoamine oxide, dimethyl (hydrogenated tallow) amine oxide, and myristyl/palmityl dimethyl amine oxide.

21. The aqueous liquid disinfectant concentrate composition according to claim 18 wherein the amine oxide is an alkyl di (hydroxy lower alkyl) amine oxide where the alkyl group has about 10–20 carbon atoms, which alkyl group may be straight chained or branched chained, and saturated or unsaturated.

22. The aqueous liquid disinfectant concentrate composition according to claim 21, wherein said alkyl di(hydroxy lower alkyl) amine oxide is selected from the group consisting of bis(2-hydroxyethyl) cocoamine oxide, bis(2-hydroxyethyl) tallowamine oxide, and bis(2-hydroxyethyl) stearylamine oxide.

23. The aqueous liquid disinfectant concentrate composition according to claim 18 wherein the constituent which improves the high temperature stability of the concentrate is urea.

24. An aqueous liquid disinfectant concentrate composition according to claim 1 which exhibits a blooming characteristic when dissolved in a greater volume of water.

25. The aqueous liquid disinfectant concentrate composition according to claim 1 which exhibits antimicrobial efficacy against one or more of the bacteria *Staphylococcus aureus, Salmonella choleraesuis,* and *Pseudomonas aeruginosa.*

26. A disinfecting composition comprising 1 part of the aqueous liquid disinfectant concentrate composition according to claim 1 diluted in at least one part of water which exhibits antimicrobial efficacy against one or more of the bacteria *Staphylococcus aureus, Salmonella choleraesuis,* and *Pseudomonas aeruginosa.*

27. A disinfecting composition comprising 1 part of the aqueous liquid disinfectant concentrate composition according to claim 1 diluted in at least 64 parts of water which exhibits antimicrobial efficacy against one or more of the bacteria *Staphylococcus aureus, Salmonella choleraesuis,* and *Pseudomonas aeruginosa.*

28. A disinfecting composition comprising 1 part of the aqueous liquid disinfectant concentrate composition according to claim 1 diluted in at least 64 parts of water which exhibits antimicrobial efficacy against at least two or more of the bacteria *Staphylococcus aureus, Salmonella choleraesuis,* and *Pseudomonas aeruginosa.*

29. A disinfecting composition comprising 1 part of the aqueous liquid disinfectant concentrate composition according to claim 1 diluted in at least 64 parts of water which exhibits antimicrobial efficacy against all three of the bacteria *Staphylococcus aureus, Salmonella choleraesuis,* and *Pseudomonas aeruginosa.*

30. A disinfecting composition comprising 1 part of the aqueous liquid disinfectant concentrate composition according to claim 1 diluted in 102 parts of water which exhibits antimicrobial efficacy against one or more of the bacteria *Staphylococcus aureus, Salmonella choleraesuis,* and *Pseudomonas aeruginosa.*

31. A disinfecting composition comprising 1 part of the aqueous liquid disinfectant concentrate composition according to claim 1 diluted in 102 parts of water which exhibits antimicrobial efficacy against at least two or more of the bacteria *Staphylococcus aureus, Salmonella choleraesuis,* and *Pseudomonas aeruginosa.*

32. An disinfecting composition comprising 1 part of the aqueous liquid disinfectant concentrate composition according to claim 1 diluted in 102 parts of water which exhibits antimicrobial efficacy against all three of the bacteria *Staphylococcus aureus, Salmonella choleraesuis,* and *Pseudomonas aeruginosa.*

* * * * *